(12) United States Patent
Preikszas et al.

(10) Patent No.: US 6,831,289 B1
(45) Date of Patent: Dec. 14, 2004

(54) DETECTOR FOR SCATTERED LIGHT

(75) Inventors: Kai-Uwe Preikszas, Aschaffenburg-Gailbach (DE); Andreas Siemens, Laatzen (DE)

(73) Assignee: Wagner Alarm-Und Sicherungssysteme GmbH, Langenhagen (DE)

( * ) Notice: Subject to any disclaimer, the term of this patent is extended or adjusted under 35 U.S.C. 154(b) by 211 days.

(21) Appl. No.: 10/130,382
(22) PCT Filed: Nov. 14, 2000
(86) PCT No.: PCT/EP00/11258
§ 371 (c)(1), (2), (4) Date: Aug. 26, 2002
(87) PCT Pub. No.: WO01/37235
PCT Pub. Date: May 25, 2001

(30) Foreign Application Priority Data

Nov. 17, 1999 (DE) .......................... 199 55 362

(51) Int. Cl.[7] .............................................. G01N 21/49
(52) U.S. Cl. ........................ 250/574; 356/436; 356/441
(58) Field of Search ................................ 250/573, 574; 73/31.03; 356/335, 336, 337, 441, 442, 436, 437, 438, 439

(56) References Cited

U.S. PATENT DOCUMENTS

| | | | | | |
|---|---|---|---|---|---|
| 3,845,480 | A | * | 10/1974 | Steinberg | ..................... 340/627 |
| 4,121,110 | A | * | 10/1978 | Solomon | ..................... 340/630 |
| 4,320,978 | A | * | 3/1982 | Sato | ............................ 356/440 |
| 4,596,465 | A | * | 6/1986 | Nagashima | ................. 356/338 |
| 4,830,494 | A | * | 5/1989 | Ishikawa et al. | ............ 356/336 |
| 4,839,529 | A | | 6/1989 | Fruengel | |
| 4,876,458 | A | * | 10/1989 | Takeda et al. | .............. 250/574 |
| 4,906,978 | A | | 3/1990 | Best | |
| 5,030,843 | A | * | 7/1991 | Wakamura | ................... 250/574 |
| 5,231,378 | A | * | 7/1993 | Dennis et al. | ............. 340/630 |
| 5,841,534 | A | | 11/1998 | Lorenz | |
| 5,929,988 | A | | 7/1999 | Ichikawa | |

* cited by examiner

Primary Examiner—Stephone B. Allen
(74) Attorney, Agent, or Firm—Volpe and Koenig, P.C.

(57) ABSTRACT

The invention relates to a detector for scattered light, especially for detecting particles in a carrier medium. Said detector comprises a housing (1) and an inlet (3) and an outlet (5) in the housing (1). The carrier medium flows through the housing between said inlet and outlet and on a flow path (7). The inventive detector also comprises a light source (9) that directs light to a scattered light centre (11) which lies on the flow path (7). The inventive detector further comprises a receiver (13) for a portion of the light which is scattered onto particles in the scattered light centre (15) and a light trap (15) for light which is not scattered in the scattered light centre (11). The aim of the invention is to improve such a detector for scattered light in such a way that compact construction and high responsiveness are guaranteed. The light trap (15) can be embodied in two ways. According to a first embodiment, the light source (9) is arranged outside the flow path (7) and the centre axis (18) of the light cone (20) pertaining to the light source (9) extends at least partially parallel in relation to or on the centre line (58) of the flow path (7). The light trap (15) allocated to the light source (9) is part of the flow channel guiding the flow path (7). According to a second embodiment, the receiver (13) is arranged outside the flow path (7). The axis (14) of the receiver extends at least partially parallel in relation to or on the centre line (58) pertaining to the flow path (7). The light trap (23) allocated to the receiver (13) is part of the flow channel guiding the flow path (7).

15 Claims, 9 Drawing Sheets

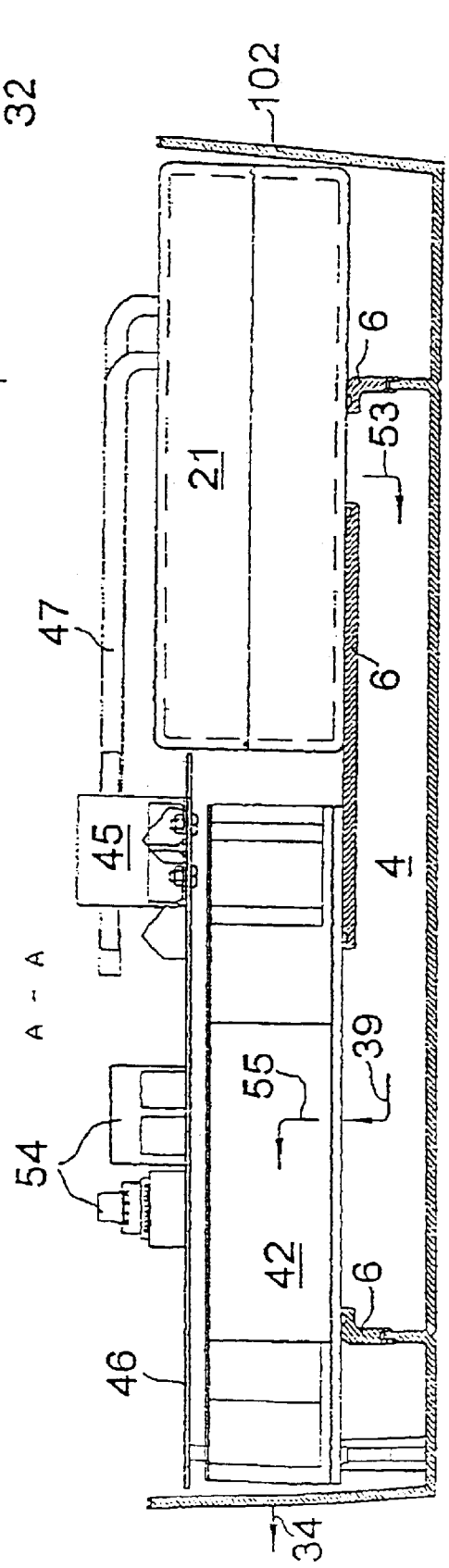

DETECTOR FOR SCATTERED LIGHT

Figure 1:
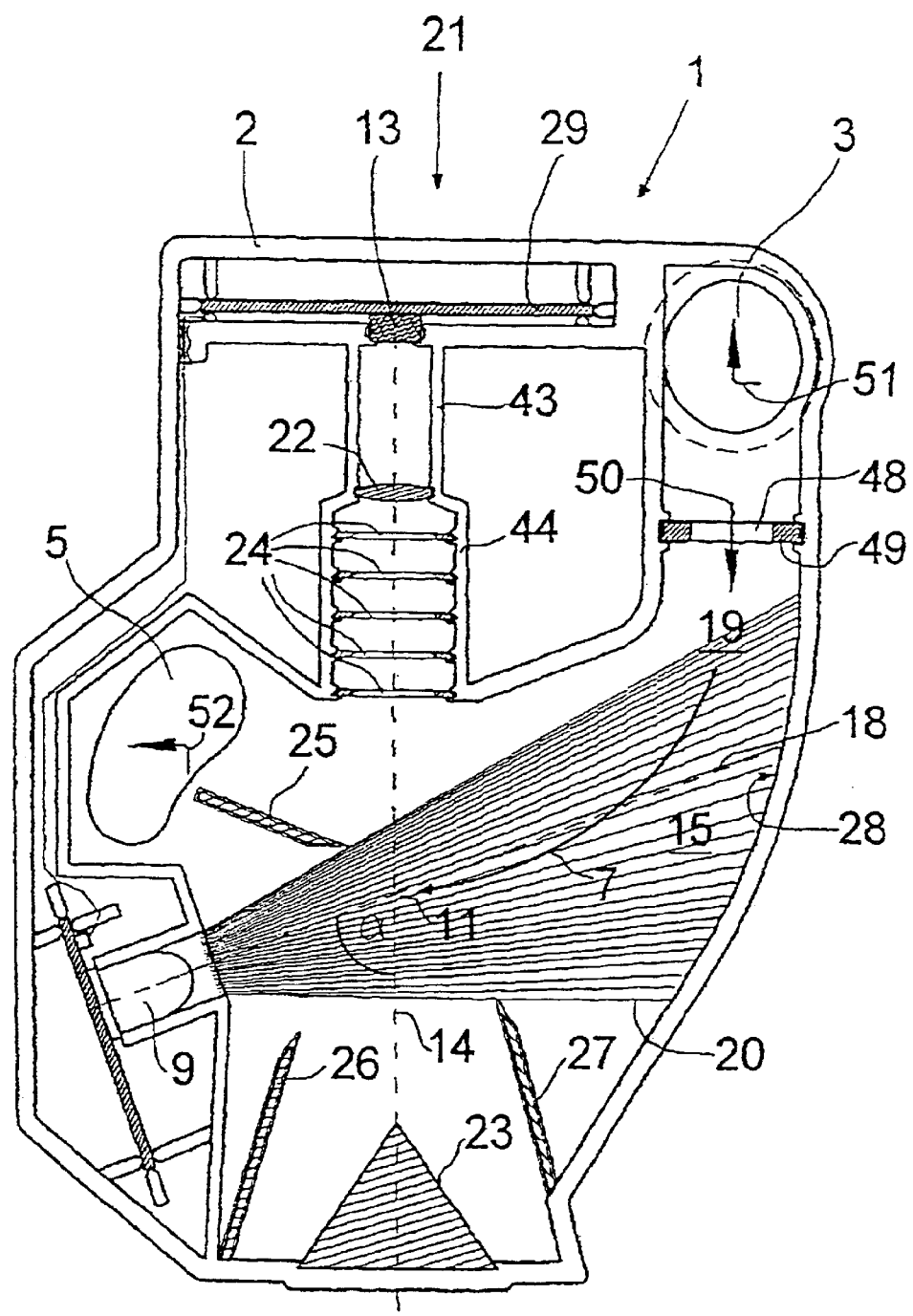

The present invention relates to a detector for scattered light as part of a hazard detector, particularly for detecting particles in a carrier medium, with a housing, with an inlet and an outlet in the housing, between which the carrier medium flows through the housing on a flow path, with a light source, which directs light to a scattered light centre, which lies on the flow path, with a receiver for a part of the light which is scattered onto particles in the scattered light centre, and with a light trap for light which is not scattered in the scattered light centre.

Such types of detectors for scattered light are known and serve, especially in aspiration fire alarm systems, to detect solid matter or liquid particles, in which the carrier medium consists of a representative partial quantity of the air of a room to be observed or of the device cooling air of a device to be observed. In an aspiration alarm system, this representative quantity of air is actively suctioned by means of a ventilator and fed into the inlet of the detector for scattered light. In devices to be monitored, such as for instance, EDP equipment or individual components thereof, as well as in similar electronic devices, such as for example, measuring, control and regulating devices, relaying equipment, and PBX devices, it is basically also possible to use the internal flow of the device-cooling air to feed a representative partial quantity of the device cooling air as carrier medium into the inlet of the detector for scattered light. An active suctioning ventilator is then unnecessary.

While the carrier medium flows through the scattered light centre on its flow path through the housing of the detector for scattered light, the light of the light source traverses the scattered light centre, and consequently, the carrier medium flowing through it, and, provided that it is not scattered onto particles in the carrier medium, is absorbed in the light trap opposite. The detector for scattered light is predominantly in this operating state. If the ray of light meets a particle, which could be, for example, a smoke particle or smoke aerosol, which provides the first indication of a fire in the initial stages, this particle diverts a fraction of the light as scattered light from its original direction, which is then absorbed by a highly light-sensitive receiver and whose intensity is measured by means of a subsequent evaluation circuit. If a certain threshold value of the light intensity is exceeded, an alarm is triggered.

Detectors for scattered light for detecting particles in a carrier medium are known from EP 0 756 703 B1 and EP 0 729 024 A2, in which the carrier medium flows through the housing in a longitudinal direction and either several light sources facing each other (EP '703) or a receiver (EP'024) are arranged on the longitudinal wall of the housing. These known detectors for scattered light are disadvantageous in that, for one thing, in light sources opposite each other, there is a risk that a majority of the light of a light source sent is reflected on the glass body of an opposite light source and a part of this reflected light then falls unintentionally on the light-sensitive receiver, consequently making it more difficult to determine the scattered light portion. On the other hand, as far as the arrangement of the receiver on the longitudinal wall of the housing goes, it is disadvantageous that this is easily dirtied, since it is placed in the flow path, which could lead to reduced responsiveness or else to an increased error rate.

Detectors for scattered light of the type mentioned at the start are known from EP 0 463 795 B1 and WO 97/42485, in which the flow path of the carrier medium runs crosswise to the longitudinal direction of the housing, and consequently, crosswise to the receiver axis. The disadvantages of these known detectors for scattered light, in particular, are that the inlets and outlets placed crosswise to the housing with the feeding pipes for the carrier medium to be connected thereto do not facilitate either a compact construction of the detector for scattered light itself or its compact arrangement within a larger detector housing, in which, for example, an air current sensor and the evaluation circuit are also accommodated.

Finally, a scattered light measuring device of the type mentioned in the beginning is known from EP 0 257 248 A2, which exhibits a funnel or paraboloid-shaped light trap for light which is not scattered in the scattered light centre, with said light trap opening towards the light source.

The purpose of the present invention is to develop a detector for scattered light, of the type mentioned at the start, i.e., with a housing, with an inlet and an outlet in the housing, between which the carrier medium flows through the housing on a flow path, with a light source, which directs light on a scattered light centre, which lies on the flow path, with a receiver for a part of the light scattered in the scattered light centre onto particles, and with a light trap for light not scattered in the scattered light centre, in such a way as to ensure a compact structural shape and yet maintain high responsiveness.

This purpose is solved in a detector for scattered light of the previously described type with two alternative and highly advantageous embodiments of the light trap, as described in patent claims 1 and 2. According to a first alternative, it is provided for the light source to be placed outside the flow path, furthermore, for the centre axis of the light cone of the light source to run, at least partially, parallel in relation to or on the centre line of the flow path, and finally, for the light trap allocated to the light source to be part of the flow channel guiding the flow path. According to a second alternative, which can also be chosen cumulatively, the receiver is arranged outside the flow path, and the receiver axis runs, at least partially, in parallel in relation to or on the centre line of the flow path, and the light trap allocated to the receiver is part of the flow channel that guides the flow path.

The two embodiments according to the invention of the detector for scattered light lie are advantageous in that the light trap allocated to the light source, as well as the light trap allocated to the receiver, is at the same time a part of the flow channel that conducts the carrier medium, for example, the representative partial quantity of the device cooling air of an EDP device, on the flow path through the detector for scattered light. In the process, it is advantageous when—as provided in an embodiment of the detector for scattered light according to the invention—the flow channel exhibits a bend where it functions as a light trap, so that the flow path of the carrier medium is diverted, and consequently, the light source "looks into empty space" towards the centre axis of its light cone and/or the receiver towards the receiver axis, as a result of which interfering reflections are excluded.

Advantageous embodiments of the invention are specified in the sub-claims.

First, two alternative embodiments of the shape of the light trap, which is allocated to the light source, are provided. According to a first alternative, this light trap is designed in such a way that, when seen from a cross sectional plane, which is vertically positioned on the receiver axis level formed by the receiver axis and the centre axis of the light cone of the light source, it exhibits the shape of a funnel, which opens towards the light source, and, cf. FIGS. 10 and 11, towards the receiver respectively. According to a second alternative, the light source is designed in such a way that—again as seen in the previously described cross-sectional plane—it approximately exhibits the shape of a parabola, whose opening points to the light source and, cf. FIGS. 10 and 11, towards the receiver. The advantages of the embodiment of the light trap according to the invention in both cases lie in the fact that light sent by the light source and not scattered in the scattered light centre is greatly reduced after repeated reflection on the walls of the light trap converging against the flow direction of the carrier medium, as a result of which it no longer affects the light-sensitive receiver, even at the highest sensitivity. As for the location of the receiver axis plane, it is to be assumed that this is horizontally aligned when the entire detector housing is on a horizontal plane. The cross-sectional shapes specified in the two alternative forms of embodiment of the light trap may involve the light trap being predominantly funnel-shaped or paraboloid-shaped, in which a sufficiently wide-open section for the entry of the carrier medium is of course provided towards the inlet.

For the shape of the light trap, it is furthermore provided for it to be designed crosswise to the described cross sectional plane, in such a way that it guides the flow path of the carrier medium in the receiver axis plane or parallel thereto in the bend through the scattered light centre to the outlet. Here, the arc-shaped curved guide on the inner wall of the light trap ensures that the deviation of the flow path from the inlet towards the scattered light centre is as free of turbulence as possible.

Since the design of the flow path for the carrier medium through the housing of the detector for scattered light has a great effect on the efficiency of the detector, the following four embodiments also deal with guiding the flow path. For one thing, it is provided for the centre axis of the light cone of the light source in the receiver axis plane to be directed towards an input channel or, alternatively, to an outlet channel, which connects in flow direction to the inlet and, with respect to the outlet channel, to the scattered light centre, and goes over to the light trap. For another, the shaping of the light trap for an increase in the sensitivity of the detector is of considerable significance. In this regard, a first embodiment of the detector for scattered light according to the invention provides for the light trap to run in an arc towards the centre line of the inlet channel and of the outlet channel respectively. Thus, the previously described attenuation of the non-scattered light portion, and with it, the detection certainty, is increased. Furthermore, it is advantageous when, in addition thereto, the flow path, after the inlet, initially runs parallel to the receiver axis before it leads through the scattered light centre towards the outlet after passing the inlet channel through the light trap in the arc. Finally, the flow path is diverted by at least 90° before the inlet and/or after the outlet, but preferably twice. Each of these embodiments contributes towards avoiding the incidence of light not being scattered onto particles in the scattered light centre towards the receiver. A measurement for the sensitivity of a detector for scattered light is namely the so-called "chamber value", which is defined by the output signal of the light receiver in case there are no particles in the scattered light centre. The repeated changes in direction in the flow path are particularly advantageous, among other things, because, as a result, it prevents outside light from penetrating the scattered light centre when there is no suction pipe or no discharge pipe connected to the housing of the detector for scattered light.

The following embodiments deal with the light source, whose arrangement, formation, and orientation likewise have a great effect on the efficiency of a detector for scattered light. In order to reach a maximum responsiveness of the detector, a high light intensity is required, with said light intensity being reached in the present detector for scattered light preferably in that the light source exhibits two light emitters, which are arranged on top of each other in the previously described cross sectional plane, and are consequently arranged at the same angle to the receiver axis. Moreover, it is advantageous for the amount of light present in the scattered light centre when the two light emitters are arranged at a slope to the receiver axis plane, in such a way that their light cones cross in the scattered light centre. Again, each of the three embodiments contributes towards increasing the responsiveness of the detector according to the invention. Thus, this detector may, for example, also be used to monitor clean rooms (e.g., chip production), in which the smallest number of particles can tie up the production of chips for several weeks. In such areas of application, it is possible to increase responsiveness, providing that the technical possibilities of the detector allow it, because, in clean rooms, there is generally no occasion for deceptive alarms due to the lack of dust and lack of moisture. The arrangement of the two light emitters one on top of the other is not known in any of the described detectors for scattered light. When using several light emitters that can also be described separately from one another as individual light sources in a spatial separation, symmetrical arrangements around the receiver axis (EP '703) or side-by-side arrangements are provided in the known detectors for scattered light. Both known arrangements of several light emitters have disadvantages. In the symmetrical arrangement around the receiver axis, there would have to be a screen for every light emitter, with said screen preventing direct light from shining on the receiver, in which the light of one emitter reflects on the screen of the other emitter, thereby unintentionally reaching the receiver, at least partially. The side-by-side arrangement of light emitters is disadvantageous in that the construction of the required screens and light traps would be more costly, and moreover, the light traps would have to be bigger in order to be able to catch both light cones.

Finally, with respect to the electromagnetic tolerance of the detector for scattered light, it may be advantageous when its housing is made of a synthetic material, which contains electrically conductive particles.

The previously described detector for scattered light may, for example, be part of a hazard detector in whose entire housing the housing of the detector for scattered light, also called "detector head", can be integrated. With respect to the housing of the detector, it is preferable for it to be made of three parts, namely one lower shell with an integrated flow channel for diverting the carrier medium into the flow direction behind the outlet of the detector head, furthermore, a cover for a part of the flow channel, and finally, an upper shell that functions as a housing cover for the danger warning system. Thus, the carrier medium flows only through the scattered light centre, the flow channel, and the suction source, which in the case of an aspiration fire alarm, could be a ventilator for suctioning the representative partial air quantity, for example. The electronics of the evaluation circuit, as well as the connecting terminals, remain outside of the sealed air conduction. A further advantage is the low manufacturing cost: the housing must be air-sealed only in the area of the air conduction, while a seal between the lower shell and upper shell is no longer necessary. The cable lead-ins also no longer need to be air-sealed. These advantages are particularly noticeable when using the detector for scattered light according to the invention in a harsh industrial environment with aggressive ambient air, if necessary. Examples for these are electroplating areas in circuit board manufacturing, lacquering lines, and battery production. In all these work areas, acids or flux accumulate in the ambient air, against which the sensitive evaluation circuit is to be protected. In this respect, it is advantageous when the flow path of the carrier medium is separated by a seal against the remaining components of the detector for scattered light, particularly against electronics and cables; a seal of the housing otherwise is not necessary. In the following, a first, a second, and a third embodiment of the detector for scattered light according to the invention will be explained more precisely using a drawing.

Figure 2:
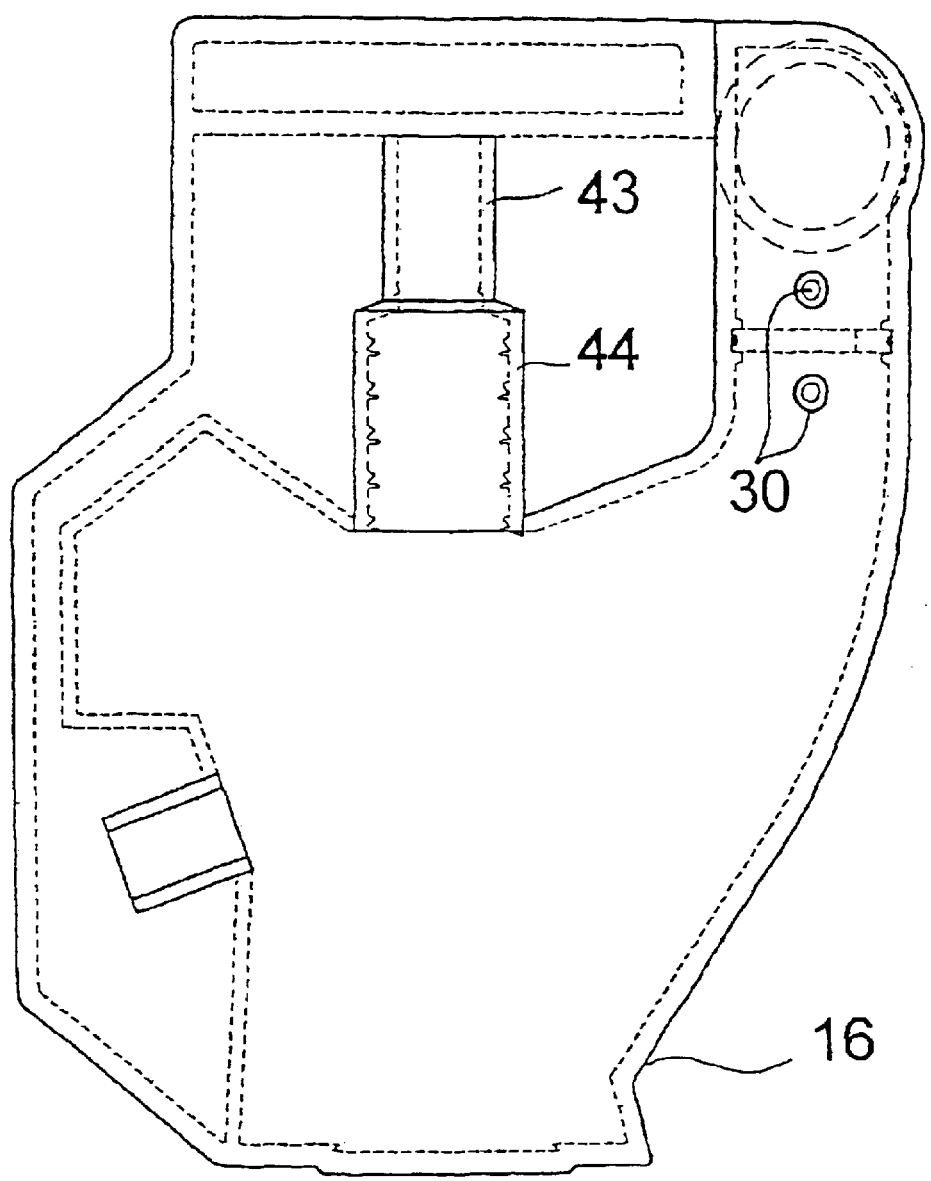
Figure 4:
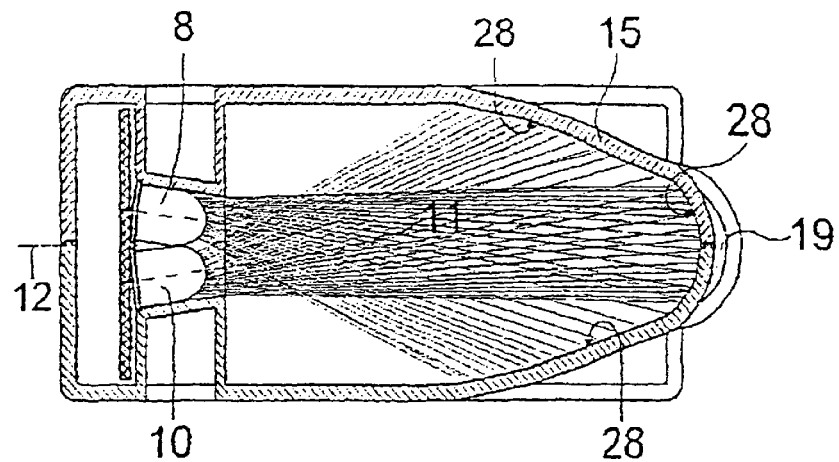
Figure 3:
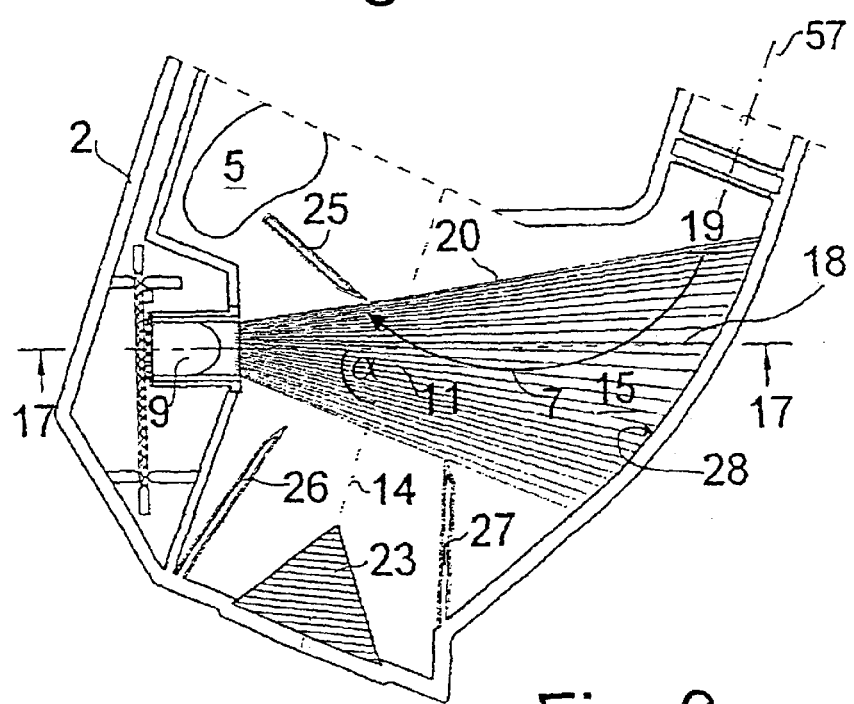
Figure 5:
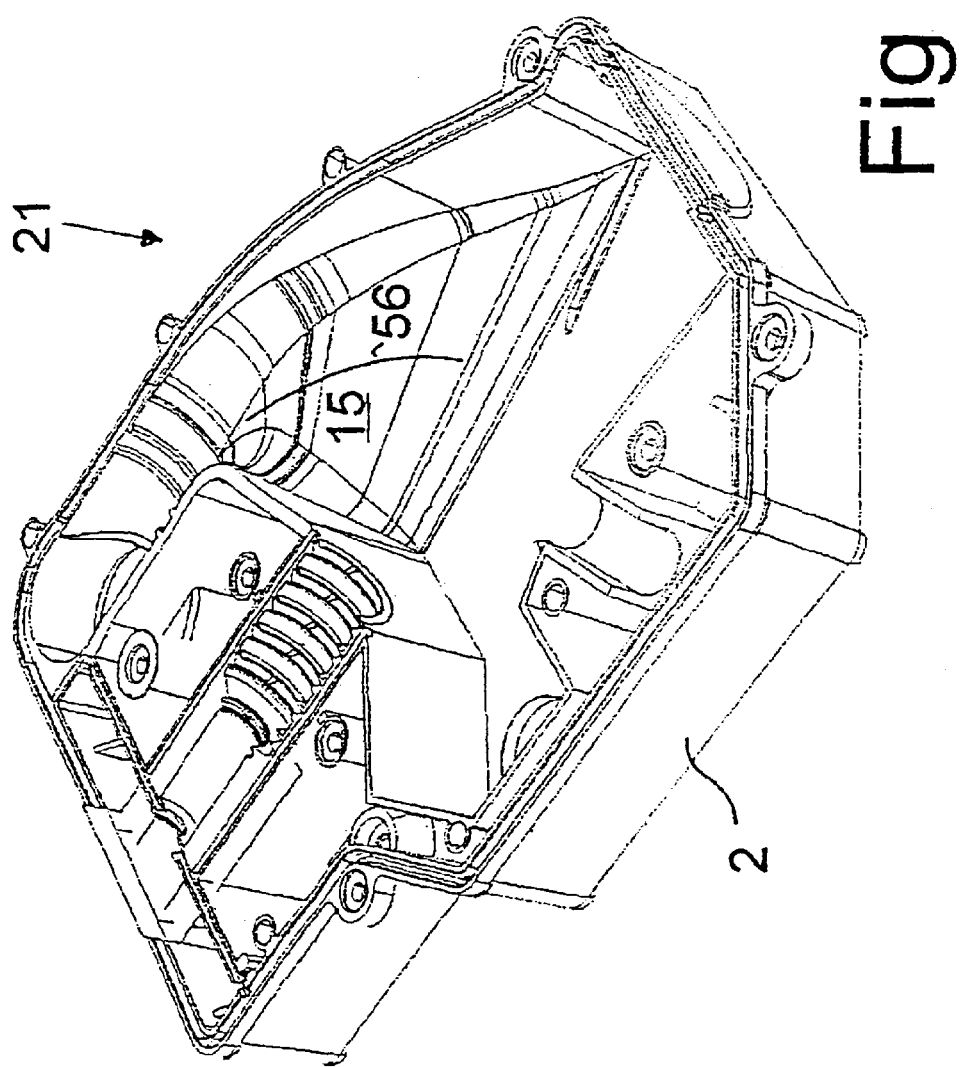
Figure 6:
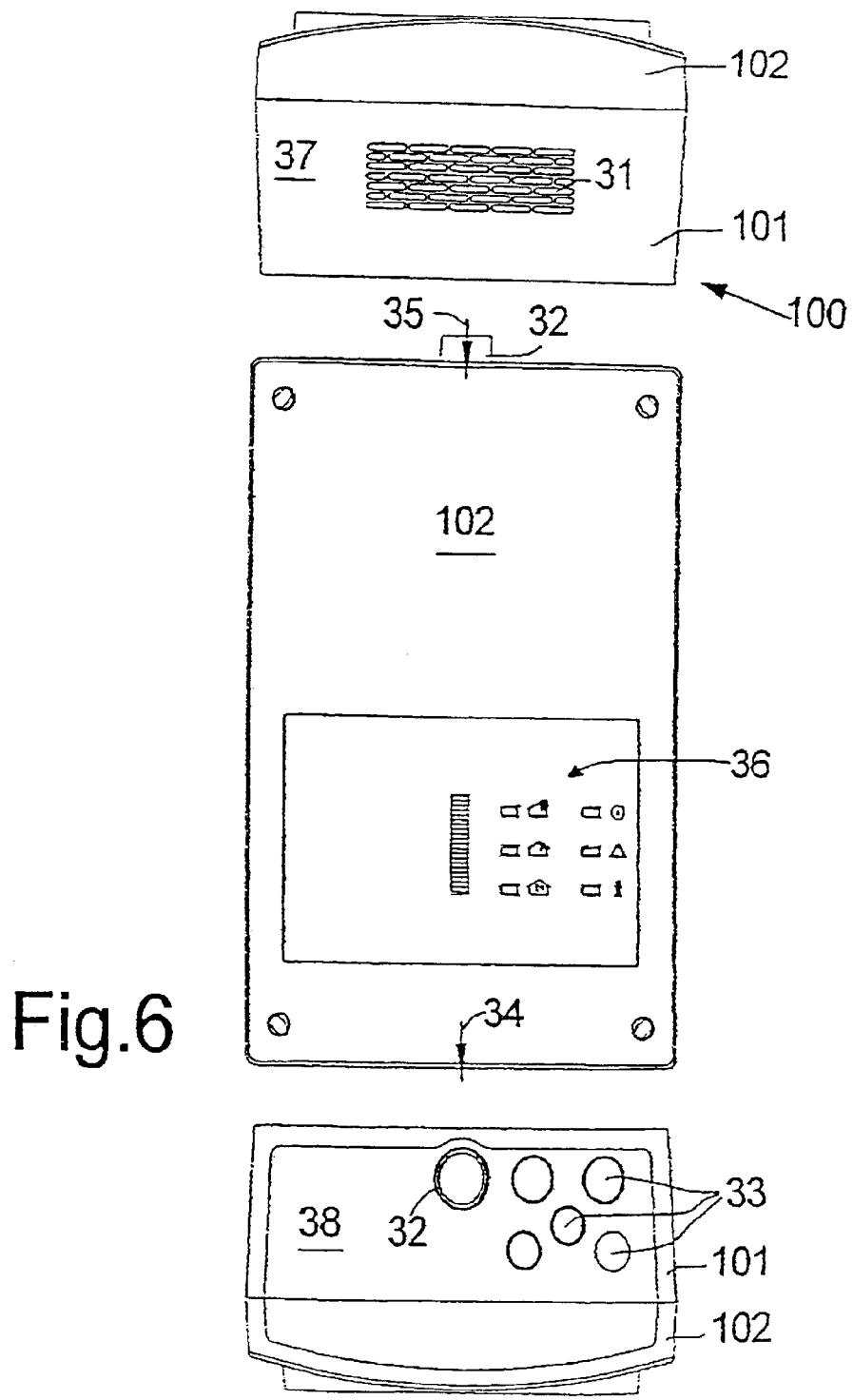
Figure 7:
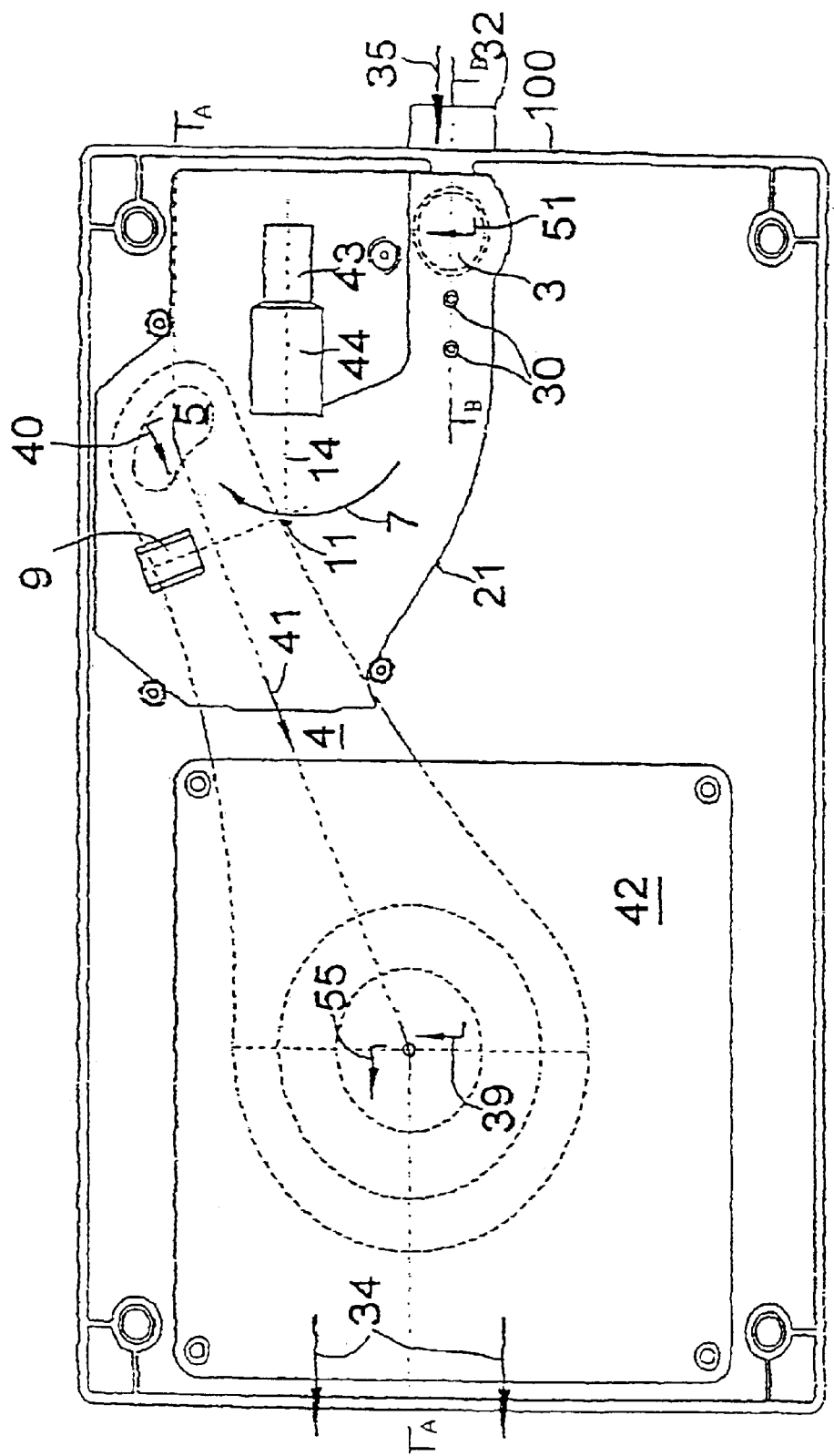
Figure 10:
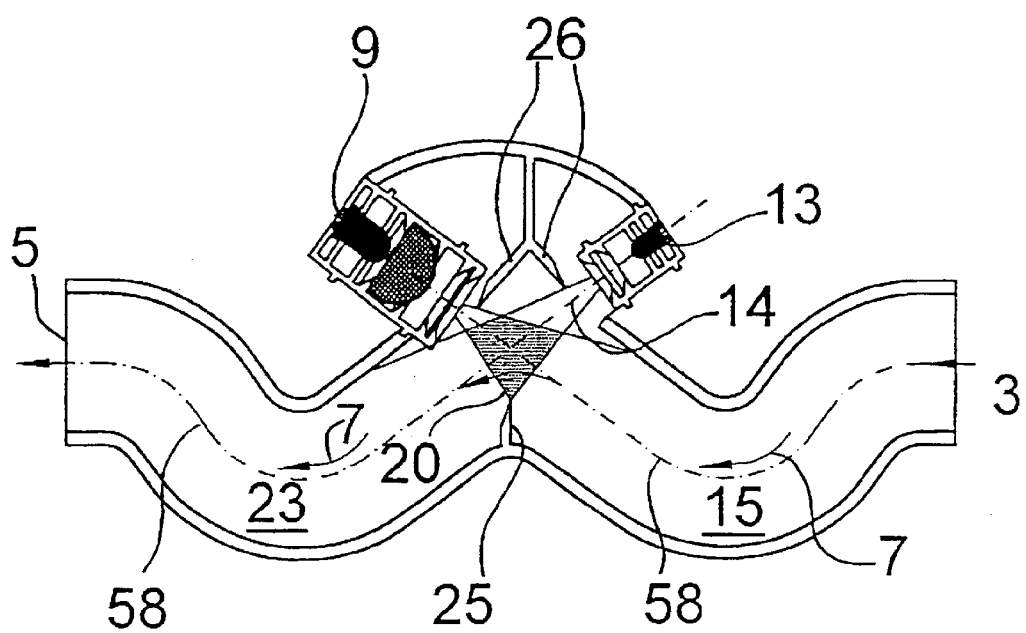
Figure 11:
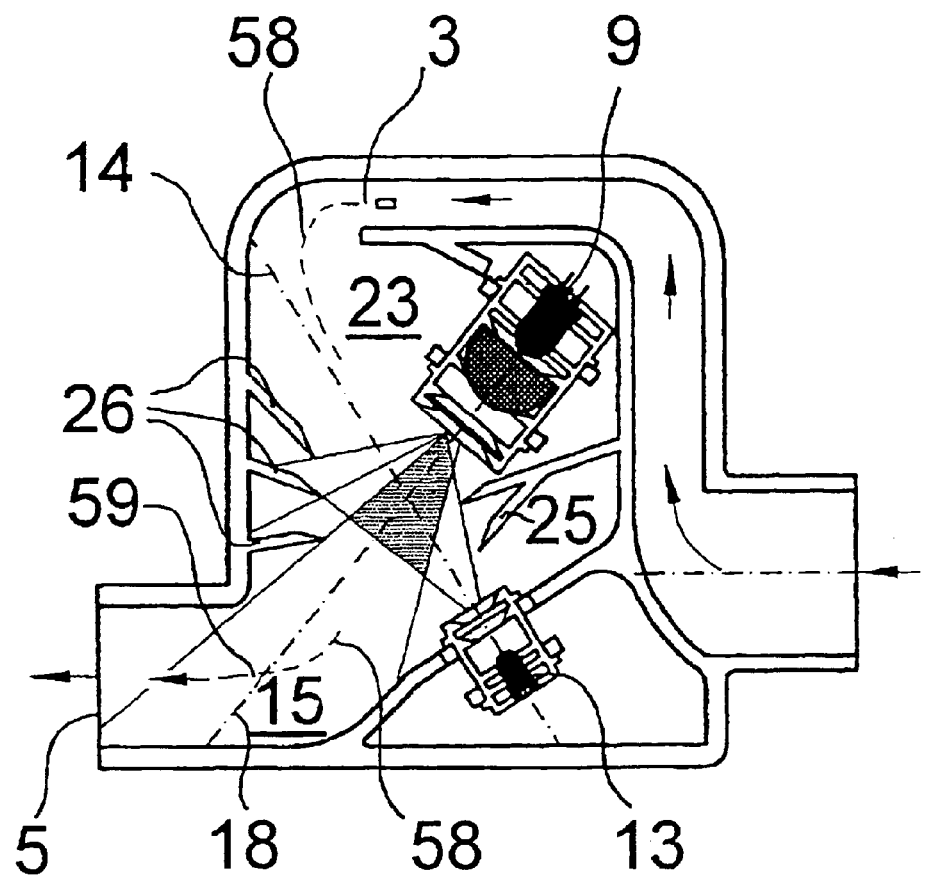

Shown are:

FIG. 1 a top view of the lower shell of the housing of the detector head of a first embodiment;

FIG. 2 a top view of the upper shell of the housing of the detector head of a first embodiment;

FIG. 3 a sectional top view of the upper shell with a view of the scattered light centre;

FIG. 4 a sectional view in the cross sectional plane 17 as per FIG. 3;

FIG. 5 a perspective representation of the housing of the detector head of the first embodiment;

FIG. 6 a view of the front side (top), a top view (centre), and a view of the rear (bottom) of a hazard detector housing;

FIG. 7 a top view of the lower shell of the hazard detector housing with flow channel, scattered light centre, and ventilator;

FIG. 8 a section along line A—A of FIG. 7;

FIG. 9 a section along line B—B of FIG. 7;

FIG. 10 a top view of the lower shell of the housing of the detector head of a second embodiment; and FIG. 11 A top view of the lower shell of the housing of the detector head of a third embodiment.

The first embodiment of a detector for scattered light described in the following is aimed at becoming part of an aspiration fire alarm device. Consequently, the carrier medium described in the patent claims is air. This air, as is usually the case for an aspiration fire alarm device, is suctioned by means of a ventilator, which will likewise be described in the following.

FIG. 1 shows a top view of the opened lower shell 2 of a housing 1 of a detector for scattered light, with the detector for scattered light shown here as the main item of a fire alarm device also being described as a detector head 21. The housing 1 of this detector head 21 exhibits an inlet 3 and an outlet 5, between which the air as carrier medium for possible particles flows through the housing 1 on a flow path 7. The detector for scattered light is furthermore equipped in a known manner with a light source 9, which directs a light cone 20 onto a scattered light centre 11, which lies on the flow path 7, furthermore with a receiver 13 in the form of a photo diode, which is placed at the rear end of a receiver housing 43 and in front of a board 29, and finally, with a light trap 15 for absorbing light not scattered in the scattered light centre 11. Connected to the receiver 13 are a lens 22 as well as a series arrangement of some screens (24), which are accommodated in a screen housing (44) connected to the receiver housing 43. A light cone 23 that tapers to a point is placed in front of the receiver 13, with said light cone serving as another light trap to protect the receiver against unintentional radiation from incident light. Furthermore, screens 25 to 27 are provided with the same purpose. The centre axis of the light cone 20 of the light source 9 is referred to as reference FIG. 18, and this centre axis 18 crosses with the receiver axis 14 in the scattered light centre 11 with the inclusion of an angle α. The light trap 15 found opposite light source 9 has, and this will be explained more precisely using FIG. 4, at least partially a funnel or paraboloid shape, and at its converging end in an arc, changes into an inlet channel 19, which, through the mediation of a disk 49 for producing differential pressure exhibiting an inside width 48, is connected with the inlet 3, and whose centre line is referred to as reference number 57. The inner wall 28 of the light trap 15 consequently runs, in the horizontal cutting plane shown here, from the inlet channel 19 in flow direction in an arc and consequently determines the flow path 7, which runs between the inlet 3 and the outlet 5. The air conduction through this detector head 21 between the inlet 3 and the outlet 5 is shown by the air conduction arrow 50 (through the opening 48 in the disk 49), 51 (90° diversion), 7 (flow path) and 52 (90° diversion). Here, the air flows through the inlet 3 in the arrow direction 51 vertically upwards initially, before it flows in a horizontal direction of movement to the scattered light centre 11 after another 90° diversion towards the air conduction arrow 50. After passing the scattered light centre 11, the air leaves the detector head 21 again through the outlet 5, towards the arrow 52 after a 90° diversion vertically downwards, where it enters the flow channel 4 (see FIG. 7).

FIG. 2 shows a top view of the upper shell 16 of the housing 1 of the detector head 21, as it fits the lower shell 2 described with the help of FIG. 1. On the top side of the upper shell 16, there are two connecting nipples 30 for an air current sensor, not shown here. Here, there is a connecting nipple in flow direction in front of the disk 49 described in FIG. 1, and a connecting nipple behind it in order to facilitate production of a differential pressure.

FIG. 3 shows a partial top view of the opened lower shell 2 of the detector head 21. All the components shown here were already explained using FIG. 1. In contrast to FIG. 1, an intersection line 17—17 is entered here in FIG. 3, which describes the cross sectional plane 17, which is vertical on the horizontal receiver axis plane 12 formed by the receiver axis 14 and the centre axis 18 of the light cone 20 of the light source 9.

FIG. 4 shows a section along line 17—17 of FIG. 3, and consequently, a view of the cross sectional plane 17 through the part of the housing, which contains the light source 9, the scattered light centre 11, and the light trap 15. Using FIG. 4, it is apparent that the light source 9 consists of two light emitters 8, 10, which are arranged on top of each other in the cross sectional plane 17, that is, the focal plane of FIG. 4. Both light emitters 8, 10 are arranged at a slant to the receiver axis plane 12, in such a way that their light cones cross in the scattered light centre 11. However, both light emitters 8, 10 take up the same angle α (cf. FIGS. 1 and 3) towards the receiver axis 14. The shape of the light trap 15 becomes clear from the sectional representation of FIG. 4: Seen from the cross sectional plane 17, that is, in the focal plane of FIG. 4, the light trap 15 is funnel-shaped or also parabolic, in which the funnel or the parabola opens towards the light emitters 8, 10 and converges towards the rear. Moreover, the inner wall 28 runs towards the rear, i.e., against the flow direction, arc-shaped outwards towards the inlet channel 19. This shape of the light trap 15 is highly advantageous because the light that meets the inner wall 28 is weakened greatly by repeated reflection, so much so that no or no appreciable portion from this direct light reaches the receiver.

FIG. 5 shows a perspective representation of the housing 1 of the detector head 21 according to FIG. 1: For the sake of a better overview, the reference figures have been left out in this representation as much as possible, and things built in, such as the light source 9, the recipient 13, the board 29 belonging to the receiver 13, the lens 22, the screens 24 to 27, the light traps 23, and the disk 49, are not shown. The sole purpose of this perspective is to provide a better illustration of the shape of the light trap 15, which in a left arc 56 tapers to the centre axis 57 of the input channel 19, and viewed in cross section, consequently forms a funnel or parabola shape.

At the start, it was pointed out that the detector head 21 with its housing 1 could be the core of a fire alarm. Aside from the detector head 21, this fire alarm exhibits the actual detector for scattered light, other components, such as a ventilator 42 (FIG. 7), an air current sensor 45 (FIG. 8), a display field 36, and various boards with control and evaluation circuits. These components are accommodated in an overall housing 100, shown in FIG. 6. This housing 100 consists of three parts, namely a lower shell 101 with an integrated flow channel 4 (FIG. 8) for diverting the air in a flow direction behind the outlet 5 of the detector head 21, furthermore of a cover 6 (FIG. 8) for a part of the flow channel 4, and an upper shell 102. The upper part of FIG. 6 shows a view of the rear wall 37 of the housing 100, in which an air outlet grid 31 is found. The centre part of FIG. 6 shows a top view of the upper shell 102 with a display field 36 and an air inlet connection piece 32 at the surface of the wall 38. At the air inlet connection piece 32, a suctioning pipe, not shown here, is connected when the detector head 21 is put into operation with the housing 100 within an aspiration fire alarm equipment. Through the air inlet connection piece 32, the representative partial quantity of the ambient air of a room to be observed or the device cooling air of a device to be monitored, mentioned at the start, is suctioned into the housing 100 in the arrow 35 direction by means of the ventilator not shown here, and after flowing through the detector head 21 (FIG. 7) and the flow channel 4 (FIGS. 7 and 8), leaves the housing 100 again in the direction of the air outlet arrow 34 through the outlet grid 31. In the lower part, FIG. 6 shows the front side 38 of the housing 100, with the air inlet connection piece 32 and some cable lead-ins 33.

FIG. 7 shows a top view of the lower shell of the housing 100, in which the detector head 21, the ventilator 42, the air current sensor 45 (FIG. 8) and the flow channel 4, as essential components, are accommodated. The air suctioned through the ventilator 42 enters towards the flow arrow 35 through the air inlet connection piece 32 first in a horizontal direction (parallel to the receiver axis 14) into the housing 100, then enters in vertical direction through the inlet 3 of the detector head 21 in the detector head 21, and afterwards again follows the flow path 7 in a horizontal direction through the scattered light centre 11 until the outlet 5 of the detector head 21, through which the air leaves the detector head in a vertical direction downwards in the direction of the flow channel 40 and enters the flow channel 4 underneath. This is shown for the most part in dotted lines in FIG. 7, since it is placed underneath the detector head 21 and the ventilator 42. In the flow channel 4, the air follows the flow arrow 41 and then enters in a vertical direction along the flow arrow 39 from below into the ventilator 42, and flows through the ventilator in the arrow 55 direction and leaves the housing 100 in the direction of the flow arrow 34 through the air outlet grid 31 (FIG. 6).

FIG. 8 shows a section through the fire alarm housing 100 along the line A—A of FIG. 7, and FIG. 9 shows a corresponding section along the line B—B of FIG. 7. Using these two sectional representations, it becomes particularly clear, aside from the arrangement of the individual elements, namely the detector head 21, the air current sensor 45, the flow channel 4, the cover 6 for the flow channel 4 and the ventilator 42, that the flow path 7 runs through the scattered light centre 11 within the detector head 21 and the flow channel 4 for diverting the suctioned air towards the ventilator 42 in different levels of the housing 100. While the ventilator 42 and the detector head 21 as well as a board 46 with the evaluation circuit 54 and the air current sensor 45 with its hose connections 47 are accommodated in the upper part of the lower shell 102 of the housing 100, the flow channel 4 flows in the lower part of the lower shell 102 and is closed air-tight against all other components, with the exception of the outlet from the detector head 21 and the entrance port into the ventilators 42 by means of the cover 6.

With the help of FIG. 9, it can be seen that the suctioned air, which goes in through the air inlet connection piece 32 in the arrow 35 direction into the lower shell 102 of the detector housing, initially flows in a horizontal direction, i.e., parallel to the receiver axis 14 (FIG. 1 or 3 or 7), then diverted by 90° vertically upwards, and immediately after, again by 90° into the horizontal position before the air goes in the direction of the arrow 50 through the inside width of the disk 49 into the inlet channel 19 (FIGS. 1 and 3) of the detector head 21. This double diversion, each time by 90°, also takes place when the air leaves the detector head 21 through the outlet 5, which is shown by the flow arrow 52 in FIGS. 1 and 40 in FIG. 7. This double diversion serves to avoid outside light from reaching the scattered light centre 11 when no suction pipe is connected to the air inlet connection piece 32 (FIG. 9).

FIG. 10 shows a second embodiment of a detector for scattered light as part of an aspiration fire alarm equipment. The lower shell of a detector head shown here in turn shows the light source 9 and the receiver 13, in which the centre axis 18 of the light cone 20 of the light source 9 and the receiver axis 14 each run crosswise (as in the first embodiment) and for a certain section, on the centre line 58 of the flow path 7, and in which the flow channel guiding the flow path 7 exhibits a bend in flow direction (see the arrows without reference figures) for the first time before the scattered light centre and a second time in the flow direction behind the scattered light centre, so that the flow path 7 undergoes a diversion each time, so that the light trap 23 allocated to the receiver 13 and the light trap 15 allocated to the light source 9 are each time arranged in the bend of the flow channel, and consequently, are a part of this flow channel.

FIG. 11 shows a third embodiment of such a detector for scattered light. Even in this embodiment, the light traps 15 and 23 respectively are each placed in a bend of the flow channel and the light source 9 and the receiver 13 respectively are equipped with their axes 18 and 14 respectively, in such a way that this runs parallel in relation to or on the centre line 58 of the flow path for a certain section, namely up to the two bends of the flow channel. Depending on the embodiment—see the first embodiment according to FIGS. 1 to 9, and the second embodiment according to FIG. 10 on the one hand, or the third embodiment according to FIG. 11 on the other hand—the centre axis 18 of the light cone 20 of the light source 9 in the receiver axis plane is directed at an inlet channel (first and second embodiment) or an outlet channel 59 (third embodiment).

What is claimed is:

1. Detector for scattered light, for detecting particles in a carrier medium, with a housing (1), with an inlet (3) and an outlet (5) in the housing (1), between which the carrier medium flows through the housing (1) on a flow path (7), with a light source (9), which directs light to a scattered light centre (11), which lies on the flow path (7), with a receiver (13) for a part of the light which is scattered onto particles in the scattered light centre (11), and with a light trap (15) for light which is not scattered in the scattered light centre (11), the light source (9) is arranged outside the flow path (7), a centre axis (18) of a light cone (20) of the light source (9) runs, at least partially, parallel in relation to or on a centre line (58) of the flow path (7), and the light trap (15) allocated to the light source (9) is a part of a flow channel guiding the flow path (7), characterized in that the light trap (15) is designed in such a way that, when seen from a cross sectional plane (17), which is vertically positioned on a receiver axis level (12) formed by a receiver axis (14) and the centre axis (18) of the light cone (20) of the light source (9), it exhibits the shape of a funnel or a parabola which opens towards the light source (9).

2. Detector for scattered light according to claim 1, characterized in that the receiver (13) is arranged outside of the flow path (7), that the receiver axis (14) runs, at least partially, parallel in relation to or on the centre line (58) of the flow path (7), and that a light trap (23) allocated to the receiver is part of the flow channel guiding the flow path (7).

3. Detector for scattered light according to claim 1, characterized in that the light trap (15) crosswise to the cross sectional plane (17) is designed in such a way that it guides the flow path (7) of the carrier medium in the receiver axis plane (12) in a bend (56) through the scattered light centre (11) to the outlet opening (5).

4. Detector for scattered light according to claim 1, characterized in that the centre axis (18) of the light cone (20) of the light source (9) in the receiver axis plane (12) is directed towards an output channel (59), which connects in flow direction to the scattered light centre (11) and goes over the light trap (15).

5. Detector for scattered light according to claim 1, characterized in that the light trap (15) in a bend (56) runs towards the centre line (57) of the input channel (19) and the output channel (59) respectively.

6. Detector for scattered light according to claim 1, characterized in that the flow path (7) is diverted by at least 90' before the inlet (3) and/or after the outlet (5), at least once.

7. Detector for scattered light according to claim 1, characterized in that the housing (1) of the detector for scattered light is made of a synthetic material, which is electrically conductive.

8. Detector for scattered light according to claim 1, characterized in that the centre axis (18) of the light cone (20) of the light source (9) in the receiver axis plane (12) is directed towards an input channel (19), which connects in flow direction to the inlet (3) and goes over the light trap (15).

9. Detector for scattered light according to claim 8, characterized in that the flow path (7), after the inlet (3), initially runs parallel to the receiver axis (14) before it leads through the scattered light centre (11) towards the outlet (5) after passing the inlet channel (19) through the light trap (15) in the arc.

10. Detector for scattered light according to claim 1, characterized in that the light source (9) exhibits two light emitters (8, 10), which are arranged on top of each other in the cross sectional plane (17) of the light trap (15).

11. Detector for scattered light according to claim 10, characterized in that the two light emitters (8, 10) are arranged at the same angle α towards the receiver axis (14).

12. Detector for scattered light according to claim 10, characterized in that the two light emitters (8, 10) are arranged at a slope to the receiver axis plane (12), in such a way that their light cones cross in the scattered light centre (11).

13. Detector for scattered light according to claim 1 as part of a hazard detector with a housing (100), characterized in that the housing (100) is made of three parts, namely one lower shell (101) with an integrated flow channel (4) for diverting the carrier medium into the flow direction behind the outlet (5), a cover (6) for a part of the integrated flow channel (4), and an upper shell (102).

14. Detector for scattered light according to claim 13, characterized in that the integrated flow channel (4) is placed in the floor region of the housing (100).

15. Detector for scattered light according to claim 13, characterized in that the flow path (7) through the scattered light centre (11) and the integrated flow channel (4) for diverting the carrier medium run into various levels of the housing (100).

* * * * *

UNITED STATES PATENT AND TRADEMARK OFFICE
CERTIFICATE OF CORRECTION

PATENT NO.      : 6,831,289 B1
DATED           : December 14, 2004
INVENTOR(S)     : Preikszas et al.

It is certified that error appears in the above-identified patent and that said Letters Patent is hereby corrected as shown below:

<u>Column 9,</u>
Line 44, delete "90'" and insert therefor -- 90° --.

Signed and Sealed this

Twenty-sixth Day of April, 2005

JON W. DUDAS
*Director of the United States Patent and Trademark Office*